United States Patent
Sapozhnikov et al.

(10) Patent No.: US 9,588,491 B2
(45) Date of Patent: Mar. 7, 2017

(54) PORTABLE ACOUSTIC HOLOGRAPHY SYSTEMS FOR THERAPEUTIC ULTRASOUND SOURCES AND ASSOCIATED DEVICES AND METHODS

(71) Applicant: University of Washington through its Center for Commercialization, Seattle, WA (US)

(72) Inventors: Oleg A. Sapozhnikov, Seattle, WA (US); Michael R. Bailey, Seattle, WA (US); Peter J. Kaczkowski, Seattle, WA (US); Vera A. Khokhlova, Seattle, WA (US); Wayne Kreider, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 681 days.

(21) Appl. No.: 13/894,333

(22) Filed: May 14, 2013

(65) Prior Publication Data

US 2013/0301383 A1  Nov. 14, 2013

Related U.S. Application Data

(60) Provisional application No. 61/646,489, filed on May 14, 2012.

(51) Int. Cl.
G03H 3/00 (2006.01)
A61B 8/00 (2006.01)
G01N 29/06 (2006.01)

(52) U.S. Cl.
CPC ............. G03H 3/00 (2013.01); A61B 8/00 (2013.01); G01N 29/0663 (2013.01); Y10S 359/901 (2013.01)

(58) Field of Classification Search
CPC ............................ G03H 3/00; Y10S 359/901
(Continued)

(56) References Cited

U.S. PATENT DOCUMENTS

| 4,415,996 A * | 11/1983 | Maynard | G03H 3/00 367/11 |
| 6,958,950 B2 * | 10/2005 | Kim | G03H 3/00 367/8 |

(Continued)

OTHER PUBLICATIONS

Sapozhnikov, O. et al., "Radiation Force of an Arbitrary Acoustic Beam on an Elastic Sphere in a Fluid," J. Acoust. Soc. Am., vol. 133(2): 661-676 (Feb. 2013).

(Continued)

*Primary Examiner* — Mark Hellner
(74) *Attorney, Agent, or Firm* — Perkins Coie LLP (57) ABSTRACT

The present technology relates generally to portable acoustic holography systems for therapeutic ultrasound sources, and associated devices and methods. In some embodiments, a method of characterizing an ultrasound source by acoustic holography includes the use of a transducer geometry characteristic, a transducer operation characteristic, and a holography system measurement characteristic. A control computer can be instructed to determine holography measurement parameters. Based on the holography measurement parameters, the method can include scanning a target surface to obtain a hologram. Waveform measurements at a plurality of points on the target surface can be captured. Finally, the method can include processing the measurements to reconstruct at least one characteristic of the ultrasound source.

18 Claims, 5 Drawing Sheets

(58) Field of Classification Search
USPC .......................................................... 367/8
See application file for complete search history.

(56) References Cited

U.S. PATENT DOCUMENTS

| | | | | |
|---|---|---|---|---|
| 2011/0172936 A1* | 7/2011 | Hald | ...................... | G01H 3/125 |
| | | | | 702/56 |
| 2013/0116982 A1* | 5/2013 | Lupien | ...................... | B06B 1/02 |
| | | | | 703/1 |

OTHER PUBLICATIONS

Tsysar, S. et al., "Improved Hydrophone Calibration by Combining Acoustic Holography with the Radiation Force Balance Measurements," Proceedings of Meetings on Acoustics, vol. 19: 055015 (Jun. 2013).

Kreider, W. et al., Characterization of a Multi-Element Clinical HIFU System Using Acoustic Holography and Nonlinear Modeling, Ultrasonics, Ferroelectrics and Frequency Control, IEEE Transactions, vol. 60(8): pages (Aug. 2013).

Shaw A, ter Haar G. Requirements for measurement standards in High Intensity Focused Ultrasound (HIFU) fields. NPL Report DQL AC 015, http://publications.npl.co.uk/npl_web/pdf/dql_ac15.pdf (2006).

Preston RC (ed), Acoustic output measurements for medical ultrasound, Springer-Verlag, ISBN 3-540-19692-7 (1991).

Kaczkowski P, Cunitz B, Khokhlova V, Sapozhnikov O, High resolution mapping of nonlinear MHz ultrasonic fields using a scanned scatterer, Proc. IEEE Ultrasonics Symposium, 982-985 (2003).

Bailey M, Khokhlova V, Sapozhnikov O, Kargl S, and Crum L. Physical mechanisms of the therapeutic effect of ultrasound (A review). Acoustical Physics 49(4), 369-388 (2003).

Dennis Gabor, 1900-1979. Nature 280 (5721): 431-433. 1979. doi:10.1038/280431a0. PMID 379651.

Sapozhnikov O, Pishchalnikov Yu, Morozov A. Reconstruction of the normal velocity distribution on the surface of an ultrasonic transducer from the acoustic pressure measured on a reference surface. Acoustical Physics 49(3): 354-360 (2003).

Sapozhnikov OA, Morozov AV, Cathignol D. Piezoelectric transducer surface vibration characterization using acoustic holography and laser vibrometry. Proceedings of 2004 IEEE UFFC 50th Anniversary Joint Conference (Montreal, Canada, Aug. 23-27, 2004), 161-164.

Sapozhnikov OA, Ponomarev AE, Smagin MA. Transient acoustic holography for reconstructing the particle velocity of the surface of an acoustic transducer. Acoustical Physics 52(3): 324-330 (2006).

Tsysar SA, Sinelnikov YD, Sapozhnikov OA. Characterization of cylindrical ultrasonic transducers using acoustic holography. Acoustical Physics 57(1), 94-105 (2011).

Kreider W, Sapozhnikov OA, Bailey MR, Kaczkowski PJ., Khokhlova VA. Holographic reconstruction of therapeutic ultrasound sources. J. Acoust. Soc. Am. 129(4, Pt2), 2403 (2011).

Kreider W, Sapozhnikov O, Khokhlova V, Farr N, Bailey M, Kaczkowski P, Partanen A, Brazzle D. Acoustic measurements and holographic reconstruction of the Philips MR-guided HIFU source. Book of Abstracts "Current and Future Applications of MR-guided Focused Ultrasound 2010", 2nd International Symposium, Oct. 17-20, 2010, Washington DC, USA, 79.

Kreider W, Sapozhnikov O, Farr N, Yuldashev P, Partanen A, Brazzle D, Bailey M, Kaczkowski P, Khokhlova V. Acoustic holography and nonlinear modeling methods to characterize the Philips MR-Guided HIFU source. Book of Abstracts of the 11th International Symposium on Therapeutic Ultrasound, International Society for Therapeutic Ultrasound (ISTD), New York, USA, 41 (2011).

Stepanishen PR, Benjamin KC. Forward and backward projection of acoustic fields using FFT methods. J. Acoust. Soc. Am. 71, 803-812 (1982).

Reibold R. Sound source reconstruction using Fouries optics. Acustica 63, 60-64 (1987).

Schafer ME, Lewin PA. Transducer characterization using the angular spectrum method, J. Acoust. Soc.Am. 85(5), 2202-2214 (1989).

Clement GT, Hynynen K. Field characterization of therapeutic ultrasound phased arrays through forward and backward planar projection. J. Acoust. Soc. Am. 108(1), 441-446 (2000). PMID 10923906.

Filonenko E, Khokhlova V. Effect of acoustic nonlinearity on heating of biological tissue induced by high intensity focused ultrasound. Acoustical Physics 47(4), 541-549 (2001).

Kaczkowski P, Andrew M, Brayman A, Kargl S, Cunitz B, Lafon C, Khokhlova V, and Crum LA. In vitro examination of nonlinear heat deposition in HIFU lesion formation. In: Therapeutic Ultrasound, Proc. 2nd Int. Symp., 341-352 (2003).

Sapozhnikov O, Khokhlova V, Cathignol D. Nonlinear waveform distortion and shock formation in the near field of a continuous wave piston source. J. Acoust. Soc. Am. 115(5, Pt1), 1982-1987 (2004).

Khokhlova VA, Bailey MR, Crum LA. Acoustic nonlinearity in derating problem for HIFU sources. In: Proc. 4th International Symposium on Therapeutic Ultrasound, Sep. 18-20, 2004, Kyoto, Japan, 134-136.

Khokhlova VA, Blanc-Benon P, Averianov MV, Cleveland RO. Propagation of nonlinear acoustic signals through inhomogeneous moving media. In: Proc. 2004 IEEE UFFC (Montreal, Canada), 533-536 (2004).

Khokhlova VA, Bailey MR, Reed J, Cunitz B, Kaczkowski P, and Crum L. Effects of nonlinear propagation, cavitation, and boiling in lesion formation by high intensity focused ultrasound in a gel phantom. J. Acoust. Soc. Am. 119(3), 1834-1848 (2006). PMID 16583923.

Averianov MV, Khokhlova VA, Cleveland RO, Sapozhnikov OA, Blanc-Benon Ph. Parabolic equation for nonlinear acoustic wave propagation in inhomogeneous moving media. Acoustical Physics 52(6), 725-735 (2006).

Khokhlova VA, Bailey MR, Reed J, Cunitz B, Kaczkowski P, Crum L. Effects of nonlinear propagation, cavitation, and boiling in lesion formation by high intensity focused ultrasound in a gel phantom. J. Acoust. Soc. Am. 119(3), 1834-1848 (2006). PMID 16583923.

Khokhlova VA, Bailey MR, Canney MS, Kaczkowski P, Crum L. Nonlinear mechanisms of heating by high intensity focused ultrasound. J. Acoust. Soc. Am. 119, 3227 (2006).

Khokhlova VA, Ponomarev AE, Averkiou MA, Crum LA. Nonlinear pulsed ultrasound beams radiated by rectangular focused diagnostic transducers. Acoustical Physics 52(4), 481-489 (2006).

Khokhlova VA, Bessonova OS, Canney MS, Bailey MR, Crum LA. Spatial distributions of acoustic parameters in high-intensity focused ultrasound fields. J. Acoust. Soc. Am. 120(5, Pt2), 3194 (2006).

Rabkin BA, Zderic V, Crum LA, Vaezy S. Biological and physical mechanisms of HIFU-Induced hyperecho in ultrasound Images, Ultrasound in Medicine & Biology 32(11), 1721-1729 (2006). PMID 17112958.

Bessonova OV, Khokhlova VA, Bailey MR, Canney MS, Crum LA. Focusing of high power ultrasound beams and limiting values of shock wave parameters. Acoustical Physics, 55(4-5), 463-473 (2009).

Crum L, Bailey M, Canney M, Hwang JH, Khokhlova V, Sapozhnikov O, The role of cavitation, nonlinear effects, and boiling in HIFU lesion production. Ultrasound Industry Association, Mar. 2009, Vancouver, Canada.

Bessonova OV, Khokhlova VA, Canney MS, Bailey MR, Crum LA. A derating method for therapeutic applications of High Intensity Focused Ultrasound. Acoustical Physics 56(3), 354-363 (2010).

Bobkova S, Gavrilov L, Khokhlova V, Shaw A, Hand J. Focusing of high intensity ultrasound through the rib cage using a therapeutic random phased array. Ultrasound in Medicine & Biology 36(6), 888-906 (2010). PMID 20510186.

Canney M, Khokhlova V, Bessonova O, Bailey M, Crum L. Shock-induced heating and millisecond boiling in gels and tissue (56) References Cited

OTHER PUBLICATIONS due to high intensity focused ultrasound. Ultrasound in Medicine & Biology 36(2), 250-267 (2010). PMID 20018433.

Crum LA, Canney M, Bailey M, Khokhlova T, Khokhlova V, Sapozhnikov O, Kreider W, Simon J. Histotripsy without cavitation. Medical Physics 38(6), 3811-3812 (2011).

Khokhlova VA, Yuldashev PV, Bessonova OV, Bailey MR, Sapozhnikov OA, Crum LA. A model of an equivalent focused piston source to characterize nonlinear ultrasound fields of 2D HIFU arrays. In: Program and Abstract Book "Current and Future Applications of MR-guided Focused Ultrasound 2010", 2nd International Symposium, Oct. 17-20, 2010, Washington DC, USA, 71.

Hall TL, Hempel CR, Wojno K, XU Z, Cain CA, Roberts WW. Histotripsy of the prostate: dose effects in a chronic canine model. Urology 74(4), 932-937 (2009). PMID 19628261.

Hall TL, Fowlkes JB, Cain CA. A real-time measure of cavitation induced tissue disruption by ultrasound imaging backscatter reduction. IEEE Trans Ultrason. Ferroelectr. Freq. Control. 54(3), 569-575 (2007). PMID 17375825.

Maxwell AD, Wang TY, Cain CA, Fowlkes JB, Sapozhnikov OA, Bailey MR, Xu Z. Cavitation clouds created by shock scattering from bubbles during histotripsy. J. Acoust. Soc. Am. 130(4), 1888-1898 (2011). PMID 21973343.

Tachibana K, Tachibana S. Albumin microbubble echo-contrast material as an enhancer for ultrasound accelerated thrombolysis. Circulation 92(5), 1148-1150 (1995). PMID 7648659.

Miller MW, Everbach EC, Cox C, Knapp RR, Brayman AA, Sherman TA. A comparison of the hemolytic potential of Optison and Albunex in whole human blood in vitro: acoustic pressure, ultrasound frequency, donor and passive cavitation detection considerations. Ultrasound in Medicine & Biology 27(5), 709-721 (2001). PMID 11397535.

Kawabata K, Sugita N, Sasaki K, Umemura S. Sonodynamic cancer treatment with cavitation-promoting agent. In: Proc. 2nd International Symposium on Therapeutic Ultrasound (Seattle, USA, 2002).

Tanter M, Thomas J-L, Coulouvrat F, Fink M. Breaking of time reversal invariance in nonlinear acoustics. Phys. Rev. E. 64, 016602 (2001). PMID 11461423.

Kaczkowski PJ, Bailey MR, Khokhlova VA, Sapozhnikov OA. A schlieren system for optical visualization of ultrasonic fields. J. Acoust. Soc. Am. 125(4, Pt2), 2742 (2009).

Tavakkoli J, Cathignol D, Souchon R, Sapozhnikov O. Modeling of pulsed finite-amplitude focused sound beams in time domain. J. Acoust. Soc. Am. 104(4), 2061-2072 (1998). PMID 10491689.

Khokhlova V, Souchon R, Tavakkoli J, Sapozhnikov O, Cathignol D. Numerical modeling of finite amplitude sound beams: Shock formation in the nearfield of a CW plane piston source. J. Acoust. Soc. Am. 110(1), 95-108 (2001).

Yuldashev PV, Khokhlova VA. Simulation of three-dimensional nonlinear fields of ultrasound therapeutic arrays. Acoustical Physics 57(3), 334-343 (2011).

Khokhlova VA, Yuldashev PV, Averiyanov MV, Bessonova OV, Sapozhnikov OA, Bailey MR. Full diffraction and parabolic axisymmetric numerical models to characterize nonlinear ultrasound fields of two dimensional therapeutic arrays. 161st Meeting of the Acoustical Society of America, Seattle, Washington, May 23-27, 2011. J. Acoust. Soc. Am. 129, 2404 (2011).

Khokhlova TD, Canney MS, Khokhlova VA, Sapozhnikov OA, Crum LA, and Bailey MR. Controlled tissue emulsification produced by high intensity focused ultrasound shock waves and millisecond boiling. J. Acoust. Soc. Am. 130(5), 3498-3510 (2011). PMID: 22088025.

* cited by examiner

PORTABLE ACOUSTIC HOLOGRAPHY SYSTEMS FOR THERAPEUTIC ULTRASOUND SOURCES AND ASSOCIATED DEVICES AND METHODS

CROSS-REFERENCE TO RELATED APPLICATION

The present application claims the benefit of U.S. Provisional Patent Application No. 61/646,489, filed May 14, 2012. The foregoing application is incorporated herein by reference in its entirety. Further, components and features of embodiments disclosed in the application incorporated by reference may be combined with various components and features disclosed and claimed in the present application.

STATEMENT REGARDING FEDERALLY-SPONSORED RESEARCH

This invention was made with government support under 5R01EB007643 awarded by the National Institutes of Health and SMST001601 awarded by the National Space Biomedical Research Institute (NSBRI). The government has certain rights in the invention.

TECHNICAL FIELD

The present technology relates generally to portable acoustic holography systems for therapeutic ultrasound sources and associated devices and methods.

BACKGROUND

High intensity focused ultrasound ("HIFU") is a rapidly developing medical technology that relies on focusing acoustic waves to treat remote tissue sites inside the body without damaging intervening tissues. HIFU can be used to treat benign and malignant tumors, dissolve blood clots, enhance drug delivery to specific sites, and ablate brain tissue causing essential tremors. A key feature of HIFU is the ability to maintain a very thin margin between treated and untreated tissue. However, the position and extent of treatment can be sensitive to many factors, including blood perfusion, tissue properties, and nonlinear acoustic propagation. In order to ensure effective treatments and to avoid adverse effects from unintended tissue injury, it is necessary to accurately determine the three-dimensional acoustic field that will be delivered to the patient. While standard practices for characterizing diagnostic ultrasound are well established, the lack of analogous metrology techniques for therapeutic ultrasound remains an impediment to broader clinical acceptance of HIFU.

Because ultrasound consists of waves, it possesses several basic features of wave physics that are of practical utility. In particular, it is possible to reproduce a three-dimensional field from a two-dimensional distribution of the wave amplitude and phase along some surface transverse to the wave propagation. This principle is widely used in optics, and the corresponding process is termed "holography." A similar approach is possible in acoustics. For acoustic pressure waves, amplitude and phase can often be measured directly with a pressure sensor, and a two-dimensional distribution of such measurements represents a hologram.

Mathematically, the hologram provides a boundary condition for the wave equation, thereby permitting the calculation of acoustic variables anywhere in three-dimensional space, including the surface of the ultrasound transducer itself. However, it can be difficult to characterize an acoustic field created by a given ultrasound transducer with a high degree of accuracy. This is because transducers can be characterized by various shapes, sizes, frequencies, operation modes, and output intensities. Many utilize an array of independent elements that can operate in both continuous-wave and pulsed modes. Corresponding acoustic fields can possess complex three-dimensional structures: aside from targeted focal regions, transducers frequently create parasitic foci and grating lobes, either due to details of the source or inhomogeneities in tissue. Standard approaches for characterizing the field structure of ultrasound sources are based on point-by-point hydrophone measurements in water. However, direct hydrophone measurement of HIFU pressures is challenging for two reasons: (1) high pressure amplitudes require large measurement bandwidths and can damage hydrophones; and (2) large treatment volumes in conjunction with multiple operation modes (such as phased-array steering of the acoustic beam) require a prohibitive number of discrete measurements. Because of these challenges, as well as the complexity of holography and the difficulty in getting reliable results, acoustic holography has not been widely adopted in therapeutic ultrasound systems.

DETAILED DESCRIPTION

The present technology relates generally to portable acoustic holography systems for therapeutic ultrasound sources and associated devices and methods. In some embodiments, a method of characterizing an ultrasound source using acoustic holography includes obtaining a transducer geometry characteristic, a transducer operation characteristic, and a hologram sensor characteristic. A control computer can be instructed to determine holography measurement parameters. Based on the holography measurement parameters, the method can include scanning a target region or surface to obtain a hologram. Waveform measurements at a plurality of points on the target surface can be captured. Finally, the method can include processing the measurements to reconstruct at least one characteristic of the ultrasound source.

Specific details of several embodiments of the technology are described below with reference to FIGS. 1-5. Other details describing well-known structures and systems often associated with therapeutic ultrasound systems have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1-5.

Figure 1:
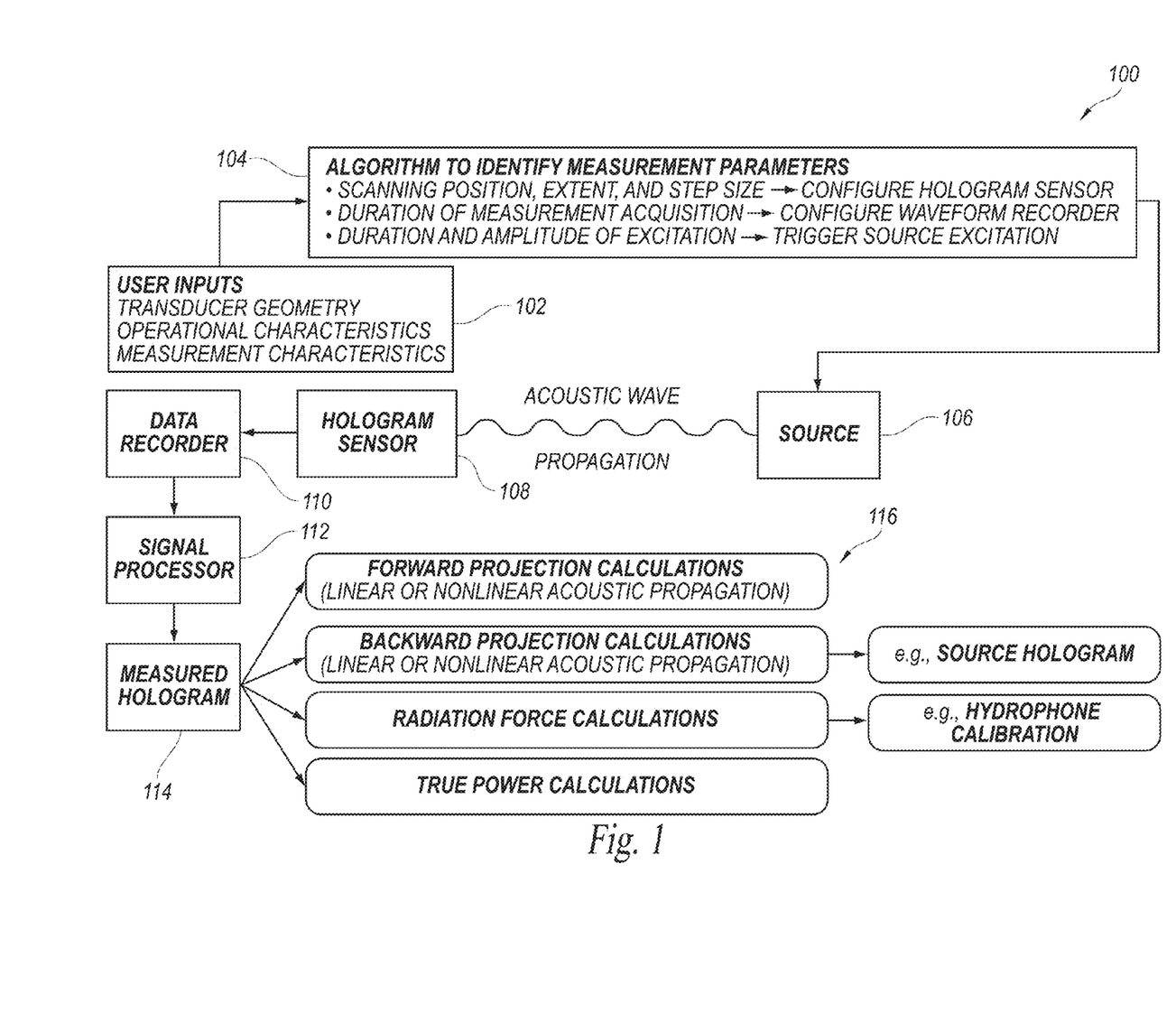
FIG. 1 is a functional schematic illustration of an acoustic holography system configured in accordance with embodiments of the technology.

FIG. 1 is a functional schematic illustration of an acoustic holography system 100 ("system 100") configured in accordance with embodiments of the technology. The system 100 can be used to simplify and standardize the implementation of acoustic holography for therapeutic ultrasound sources. FIG. 1 illustrates the functional sequence whereby the system 100 can be used to receive relevant user inputs, determine holography measurement parameters, acquire these measurements, and perform subsequent analyses and calculations.

The system 100 can include an input device 102 capable of receiving inputs related to system components and/or operational characteristics. For example, in some embodiments, the input device 102 can receive inputs related to the geometry of an ultrasound transducer, the transducer's operational characteristics, and details of the hologram measurement apparatus. The transducer geometry inputs can include the size and/or shape of a radiating surface on the transducer and an approximate orientation of the transducer in three-dimensional space. The operational characteristics shared with the input device 102 can include, for example, the frequency and Q-factor that describe the transducer's resonant characteristics, as well as the regime in which the transducer is to be characterized. The transducer's operational characteristics can further include a characterization as either continuous-wave (CW) or transient vibration, and output intensities that are consistent with either linear or nonlinear acoustic propagation between the transducer and measurement sites. Inputs related to the measurement apparatus can include, for example, the size of a hydrophone sensing region, a hydrophone bandwidth, a geometry of a test tank and associated fixturing, a liquid temperature in a test tank, and a reference position relative to a transducer at which a hydrophone is initially located. In some embodiments, details of the measurement apparatus can be defined by the user. The input device 102 can receive these inputs as user inputs, from a stored input source (e.g., a database) or directly from system components. In other embodiments, the input device 102 may include different features and/or have a different arrangement.

The input device 102 can pass the inputs to a control computer 104 capable of implementing an algorithm to identify hologram measurement parameters. The algorithm can utilize numerical and/or experimental studies of amplitude and phase distributions of acoustic fields radiated by representative clinical therapeutic ultrasound sources. For example, the control computer 104 and algorithm may be configured to determine parameters such as the location and extent of a surface where measurements are to be acquired, the spacing between individual measurements on the surface, the temporal pulse time window relative to excitation of the transducer during which each pressure measurement is captured, and/or a reverberation (blanking) period. Using these and/or other parameters, hologram measurements can be recorded and subsequent analysis and calculations can be performed. The control computer 104 can thus identify standard parameters for a given arrangement of a holography system.

The control computer 104 or other controller can instruct an ultrasound source 106 to generate and amplify a voltage waveform used to excite a transducer. The ultrasound source 106 can generate acoustic wave propagation between the transducer and a measurement site. A hologram sensor 108 can measure the acoustic waveforms (e.g., pressure or velocity) at points spanning a two-dimensional measurement region that may be generally oriented to be approximately perpendicular to the axis of the acoustic beam being measured. The hologram sensor 108 can comprise other arrangements in further embodiments. A data recorder 110 can capture the acoustic waveforms measured by the hologram sensor 108. The measurement parameters determined by the algorithm implemented by the control computer 104 can be used to obtain, record, and analyze the hologram. For example, the scanning position, scanning extent, and step size determined by the algorithm can be used to configure the hologram sensor 108. The duration of measurement acquisition determined by the algorithm can be used to configure the data recorder 110. And the duration and amplitude of excitation as determined by the algorithm can instruct the excitation of the ultrasound source 106.

A signal processor 112 can receive the acoustic waveform data from the data recorder 110 and can perform signal processing on the data in order to define and output a measured hologram 114 from the raw measurements. As will be described in further detail below, based on the measured hologram 114, the system 100 can utilize a control computer (i.e., the control computer 104 or another control computer) to generate one or more characteristics 116 of the ultrasound source 106. For example, the characteristics 116 can include forward and backward projections (using linear or nonlinear acoustic propagation), radiation force calculations for specified targets, and calculations of the true acoustic power. As will be discussed in further detail below with reference to FIGS. 3A-3D, backward projections can determine the vibrations on the surface of the transducer, which may be referred to as a "source hologram." In some embodiments, the holography system 100 can auto-focus the source hologram (e.g., angle and distance) for alignment. As will be discussed in further detail below with reference to FIG. 5, the radiation force calculations can be used for hydrophone calibration. In some embodiments, a series of holograms recorded over a range of output levels can be used to fully characterize source output levels. In further embodiments, additional or alternate characteristics can be calculated.

The control computer 104, processor, or other computing devices on which the acoustic holography system 100 is implemented may include a central processing unit, memory, input devices (e.g., keyboard and pointing devices), output devices (e.g., display devices), and storage devices (e.g., disk drives). The memory and storage devices are computer-readable media that may be encoded with computer-executable instructions that implement the object permission enforcement system, which means a computer-readable medium that contains the instructions. In addition, the instructions, data structures, and message structures may be stored or transmitted via a data transmission medium, such as a signal on a communications link and may be encrypted. Various communications links may be used, such as the Internet, a local area network, a wide area network, a point-to-point dial-up connection, a cell phone network, and so on.

Embodiments of the acoustic holography system may be implemented in and used with various operating environments that include personal computers, server computers, handheld or laptop devices, multiprocessor systems, microprocessor-based systems, programmable consumer electronics, digital cameras, network PCs, minicomputers, mainframe computers, computing environments that include any of the above systems or devices, and so on.

The acoustic holography system may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

Figure 2A:
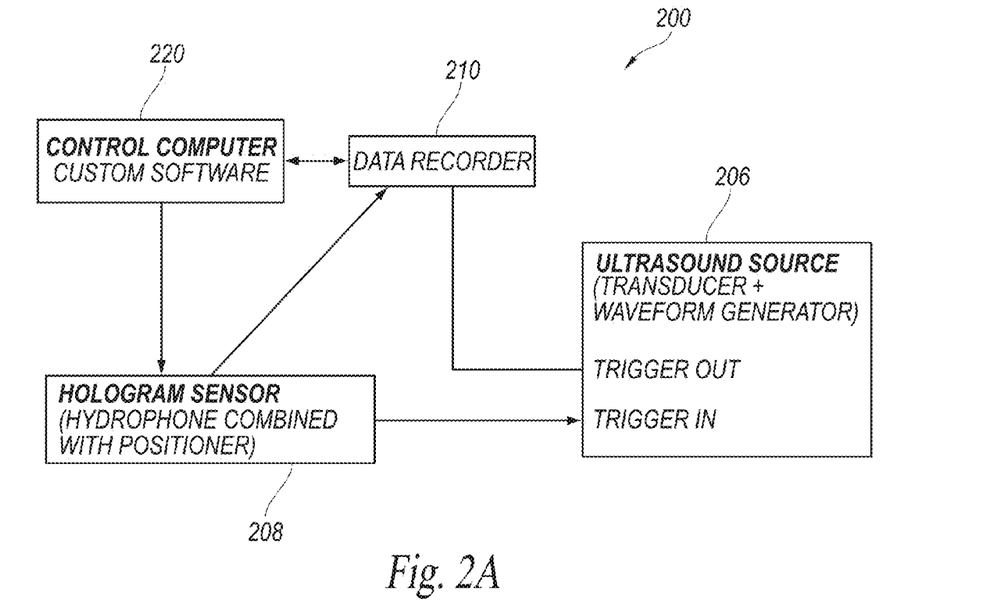
FIG. 2A is a schematic illustration of an acoustic holography system configured in accordance with embodiments of the technology.
Figure 2B:
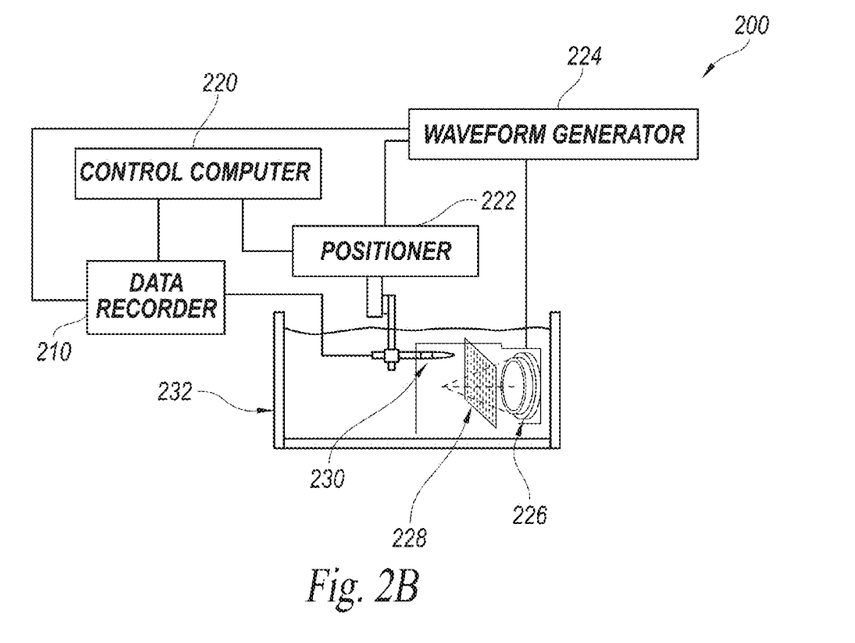
FIG. 2B is a partially schematic illustration of the acoustic holography system of FIG. 2A configured in accordance with embodiments of the technology.

FIG. 2A is a schematic illustration of an acoustic holography system 200 ("system 200") configured in accordance with embodiments of the technology. FIG. 2B is a partially schematic illustration of the system 200 of FIG. 2A. Referring to FIGS. 2A and 2B together, the system 200 embodies several functional features discussed above with reference to FIG. 1. For example, the system 200 includes an ultrasound source 206 capable of propagating acoustic waves sensed by a hologram sensor 208 and recorded by a data recorder 210. In some embodiments, the ultrasound source 206 includes a transducer 226 and a waveform generator 224. The transducer 226 can radiate sound while the waveform generator 224 can generate and amplify the voltage waveform used to excite the transducer 224. In further embodiments, the ultrasound source 206 can comprise another device having "trigger in" and "trigger out" capabilities that enable the transducer excitation to be synchronized with the position of the hologram sensor 208 and the waveform acquisition by the data recorder 210.

The hologram sensor 208 can include one or more hydrophones 230 and a positioner 222. As discussed above, the hologram sensor 208 can measure acoustic waveforms (pressure or velocity) at points spanning a two-dimensional region. The hologram sensor 208 can take on various arrangements including: a two-dimensional array of independent hydrophones 230; a one-dimensional array of independent hydrophones 230 in conjunction with a repeatable source and the positioner 222 that is automated in at least one dimension; or a single hydrophone 230 in conjunction with a repeatable source and the positioner 222 that is automated in at least two dimensions. In some embodiments, the hologram sensor 208 measures the acoustic waveforms on a measurement surface 228. The measurement surface 228 may comprise a two-dimensional surface generally transverse to the wave propagation. In some embodiments, the hologram sensor 208 can measure the acoustic waveforms in a test tank 232 filled with water or other media. In particular embodiments, the system 200 can include a thermometer in or proximate to the tank 232 to record the temperature of the acoustic medium in the test tank 232 to account for changes in sound speed during measurement acquisition.

In some embodiments, the approximate position of the hologram sensor 208 relative to the transducer 226 need not be known with a high degree of accuracy because the measured hologram captures the full three-dimensional acoustic field, and the position of the transducer 226 can be inferred from backward projection calculations. Explicit requirements regarding the positional accuracy with which the hologram sensor 208 is interfaced to the transducer 226 may be warranted to meet strict measurement standards. However, in many cases it can be sufficient to orient the hologram sensor 208 to be perpendicular to the acoustic axis of the transducer 226 ("by eye"); then the distance between hologram sensor 208 and the transducer 226 can be estimated by identifying the position of the acoustic focus or by measuring time of flight.

A control computer 220 can instruct the various components in the manner described above to generate acoustic waves, sense, receive, record, measure, and/or analyze a measured hologram, and make calculations based on this measured hologram. For example, based on the measured hologram, the system 200 can utilize the control computer 220 to generate one or more of the characteristics of the source 206 described above: forward and backward projections, radiation force calculations for specified targets, and calculations of the true acoustic power. In further embodiments, additional or alternate characteristics can be calculated by the control computer 220.

Figure 3A:
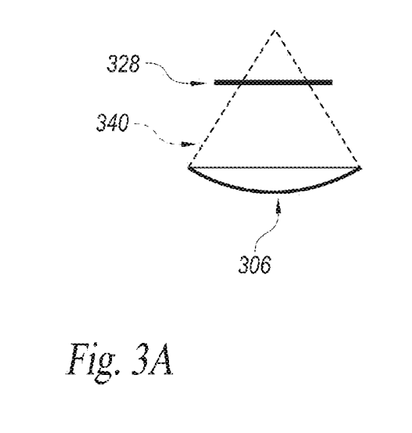
FIG. 3A is side view of a measurement configuration for a focused ultrasound source configured in accordance with embodiments of the technology.

FIG. 3A is side view of a measurement configuration for a focused source configured in accordance with embodiments of the technology. The arrangement illustrated in FIG. 3A can be used to obtain a source hologram in the manner described above with reference to FIGS. 1-2B. For example, the system 200 discussed above with reference to FIGS. 2A and 2B can be used to obtain a measured hologram on a scan plane measurement surface 328. The measurement surface 328 can comprise a two-dimensional surface generally transverse to an acoustic wave beam 340. In various embodiments, scan points can be in a rectangular grid or non-rectangular pattern on a plane. The measured hologram on the measurement surface 328 can be used in calculations to determine the source hologram representing vibrations on the surface of an array transducer 306. In some embodiments, the holography system 200 can auto-focus the source hologram (e.g., angle and distance) for alignment. The source hologram may be useful in itself to provide a record of source performance for quality assurance purposes. In addition, source holograms and measured holograms may be used to define boundary conditions for linear or nonlinear acoustic propagation calculations. Propagation calculations can determine vibrations at the transducer surface as a source hologram, or in a three-dimensional pressure field in an acoustic medium with known properties, such as water or tissue.

Figure 3B:
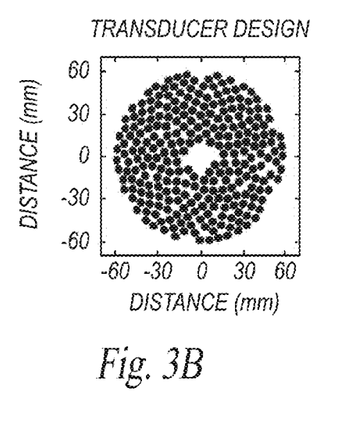
FIG. 3B is a graphical representation of a multi-element, clinical array transducer for use with the measurement configuration of FIG. 3A.
Figure 3C:
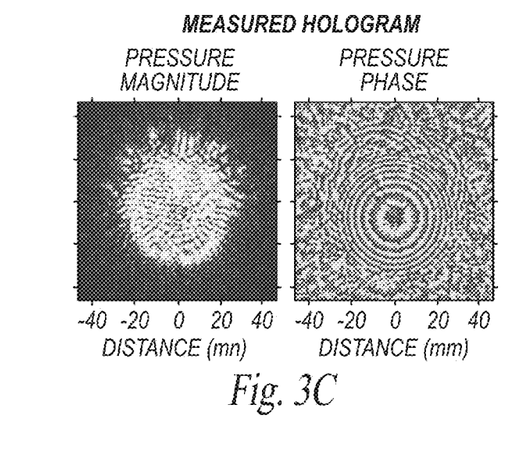
FIG. 3C is a graphical representation of a measured hologram for the transducer of FIG. 3B in accordance with embodiments of the technology.
Figure 3D:
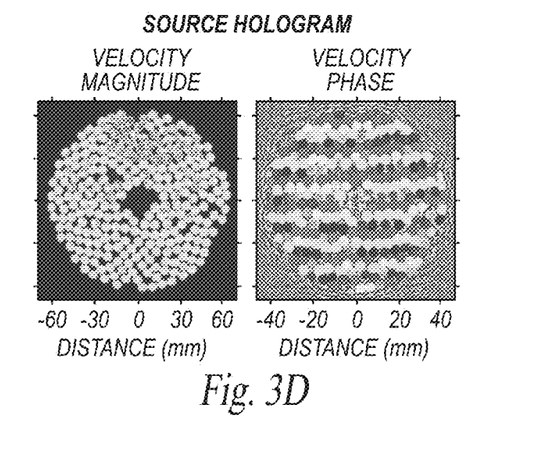
FIG. 3D is a graphical representation of a source hologram calculated by a backward projection from the measured hologram in FIG. 3C in accordance with embodiments of the technology.

FIG. 3B is a graphical representation of a surface of the multi-element, clinical array transducer 306 shown in FIG. 3A. FIG. 3C is a graphical representation of a measured hologram (i.e., the hologram measured on the measurement surface 328) for the transducer 306 of FIG. 3A in accordance with embodiments of the technology. FIG. 3D is a graphical representation of a source hologram calculated by a backward projection from the measured hologram in FIG. 3C in accordance with embodiments of the technology. Both magnitude and phase components of the source hologram (shown in FIG. 3D) illustrate the expected pattern of array elements corresponding to the transducer array shown in FIG. 3B.

Aside from acoustic propagation, other types of calculations based on measured holograms can be directly relevant to therapeutic sources. For example, the measured hologram can be used to calculate the true acoustic output power of the source and calculate the radiation forces that would occur if the acoustic beam impinged on particular targets. Acoustic output power can be estimated from a spatial distribution of pressure magnitude measurements. However, such an approach typically assumes that the acoustic beam comprises a plane wave and is not correct for an arbitrary acoustic beam (such as that generated by a focused source). Because a measured hologram incorporates phase information, it can be used to calculate the true power of an arbitrary beam, and this calculation can be performed efficiently using an angular spectrum approach.

In addition, measured holograms can be used to calculate radiation forces on target objects, which may be useful in itself (e.g., for pushing kidney stones). Further, because a hologram permits calculation of the radiation force on a perfectly absorbing target, a hydrophone's sensitivity at a single frequency can be calibrated by comparing a measured hologram to analogous measurements made with a radiation force balance. Because the uncertainty associated with radiation force balance measurements can be significantly less than that associated with laser vibrometry at megahertz frequencies, single-frequency hydrophone calibrations using an approach based on holography may be comparable to or better than primary calibrations that rely on laser vibrometry.

Figure 4:
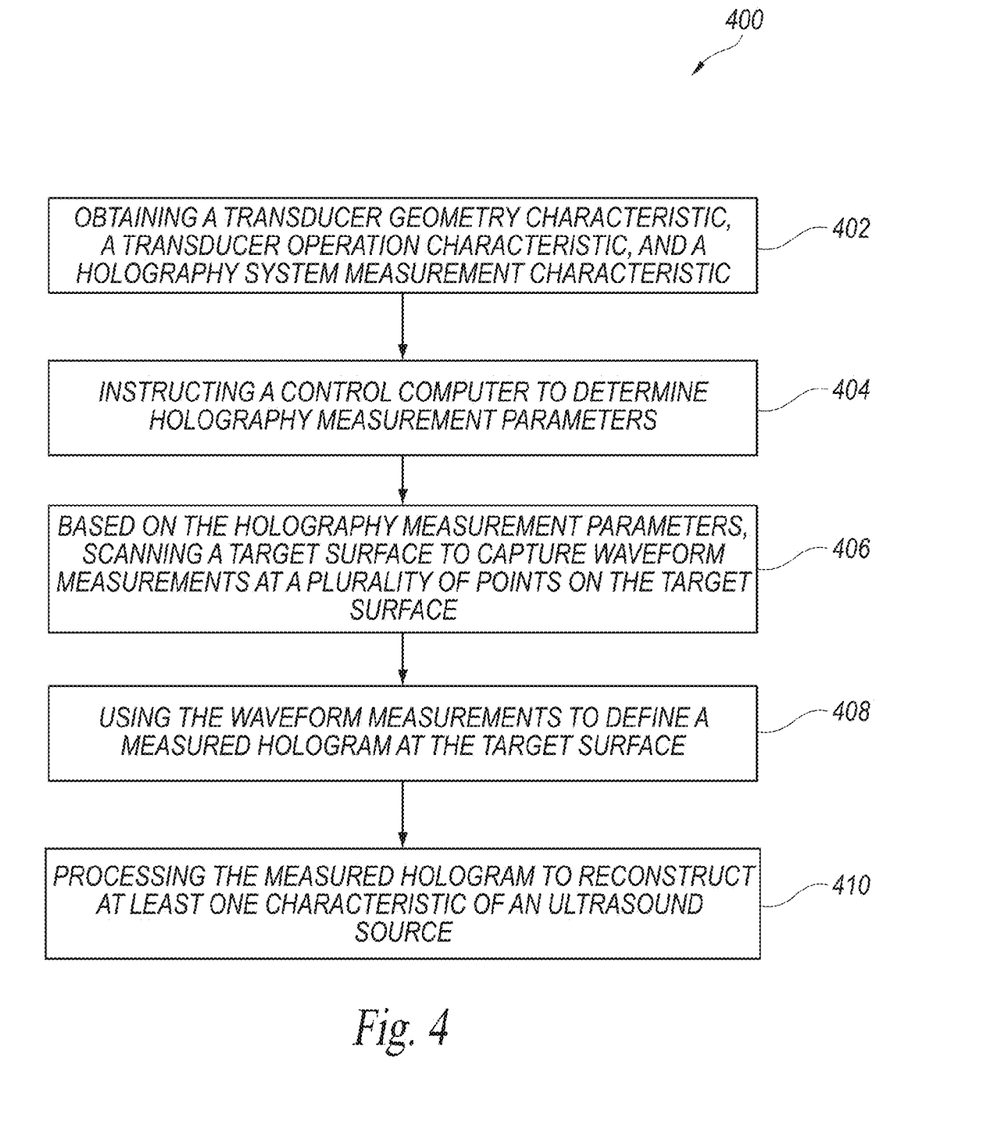
FIG. 4 is a block diagram illustrating a method of characterizing an ultrasound source using acoustic holography in accordance with embodiments of the technology.

FIG. 4 is a block diagram illustrating a method 400 of characterizing an ultrasound source using acoustic holography in accordance with embodiments of the technology. At block 402, the method 400 can include obtaining a transducer geometry characteristic, a transducer operation characteristic, and a holography system measurement characteristic. In some embodiments, obtaining a transducer geometry characteristic comprises obtaining at least one of an aperture size, planar or curvature characteristic, orientation, or shape of a radiating transducer. Obtaining a transducer operation characteristic can comprise obtaining at least one of a linear, nonlinear, pulsing, continuous, spatial extent, Q-factor, or operating frequency characteristic of a radiating transducer. In some embodiments, obtaining a holography system measurement characteristic comprises obtaining at least one of a size of a hydrophone sensing region, a hydrophone bandwidth, a geometry of a test tank, a liquid temperature in the test tank, or a reference position relative to a transducer at which the hydrophone is initially located.

At block 404, the method 400 includes instructing a control computer to determine holography measurement parameters. In some embodiments, the measurement parameters can include at least one of a scanning position, a scanning extent, or step size of a hologram sensor, a duration of measurement acquisition of a data recorder, or a duration or amplitude of excitation of the ultrasound source.

Based on the holography measurement parameters, at block 406 the method 400 includes scanning a target surface to capture waveform measurements at a plurality of points on the target surface. In some embodiments, a two-dimensional target surface is scanned. The scanning can be continuous, pulsed, or otherwise intermittent. At block 408, the method 400 includes using the waveform measurements to define a measured hologram of the acoustic field on the target surface.

At block 410, the method 400 includes processing the measured hologram to reconstruct at least one characteristic of the ultrasound source. In some embodiments, holograms are used to define boundary conditions for calculating three-dimensional acoustic field characteristics of the ultrasound source. In particular embodiments, such calculations are performed by applying at least one of a Rayleigh integral, Helmholtz-Kirchoff integral, Khokhlov-Zabolotskaya-Kuznetsov ("KZK") equation, or a Westervelt equation. These calculations can determine pressure waveforms (including shock waves), estimate heating rates, and/or account for tissue attenuation by scaling the source amplitude. The method 400 can be performed for linear or nonlinear acoustics, and for uniform or nonuniform media.

In some embodiments, processing the measured hologram to reconstruct a characteristic of the ultrasound source comprises determining at least one of an acoustic output power of the ultrasound source or a radiation force that would occur if an acoustic beam from the ultrasound source impinged on a particular target. In a particular embodiment, for example, the radiation force can be used in conjunction with an independent radiation force balance measurement to calibrate a hydrophone's sensitivity at a single frequency.

Figure 5:
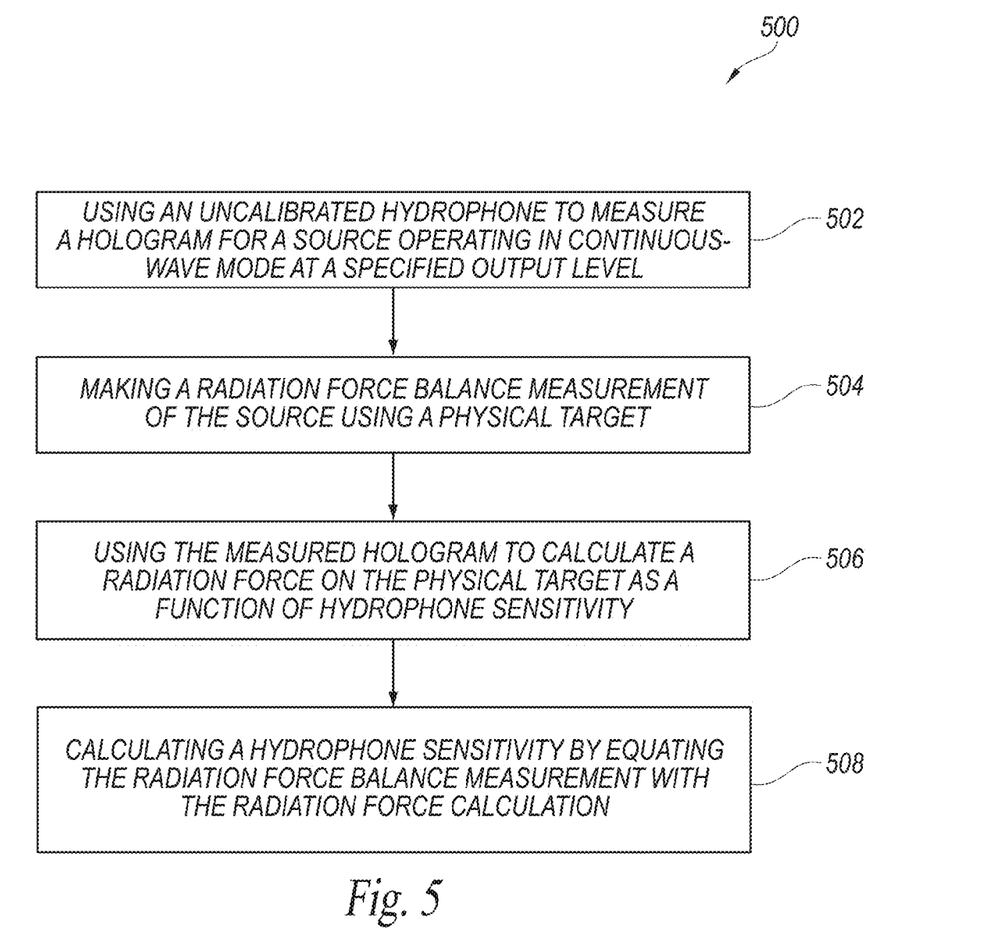
FIG. 5 is a block diagram illustrating a method of calibrating a hydrophone in accordance with embodiments of the technology.

FIG. 5 is a block diagram illustrating a method 500 of calibrating a hydrophone in accordance with embodiments of the technology. In several embodiments, for example, the hydrophone sensitivity can be calibrated at a single frequency. At block 502, the method 500 can include using an uncalibrated hydrophone to measure a hologram for a source operating in continuous-wave mode at a specified output level. In some embodiments, the hologram is measured using the method 400 described above with reference to FIG. 4. At block 504, the method 500 includes making a radiation force balance measurement of the source using a particular physical target. In some embodiments, making a radiation force balance measurement comprises making a radiation force balance measurement under identical pulse waveform conditions as the hologram was measured.

At block 506, the method 500 includes using the measured hologram to calculate a radiation force as a function of hydrophone sensitivity for the physical target used in the radiation force balance measurements. At block 508, the method 500 includes calculating a hydrophone sensitivity by equating the radiation force balance measurement with the radiation force calculation based on the measured hologram.

The technology disclosed herein offers several advantages over traditional field-mapping systems. For example, the present technology implements computer-readable instructions to determine suitable measurement parameters for a hologram, and provides additional capabilities for using the measured hologram as an input to practical calculations. Further, in some embodiments, the holography systems described herein can be portable to enable their use as a standard measurement tool for therapy transducers in both clinical and research environments. Additionally, the holography systems described herein can provide accelerated measurement acquisitions, such as by continuous scanning, use of a hydrophone array, or by capturing of fewer points and performing calculations with a reduced hologram quality.

From the foregoing it will be appreciated that, although specific embodiments of the technology have been described herein for purposes of illustration, various modifications may be made without deviating from the spirit and scope of the technology. Further, certain aspects of the new technology described in the context of particular embodiments may be combined or eliminated in other embodiments. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A method of characterizing an ultrasound source using acoustic holography, the method comprising:
    obtaining a transducer geometry characteristic, a transducer operation characteristic, and a holography system measurement characteristic,
    wherein obtaining the transducer geometry characteristic comprises obtaining at least one of an aperture size, planar or curvature characteristic, orientation, or shape of a radiating transducer;
    instructing a control computer to determine holography measurement parameters;
    based on the holography measurement parameters, scanning a target surface to capture waveform measurements at a plurality of points on the target surface;
    using the waveform measurements to define a measured hologram at the target surface; and
    processing the measured hologram to reconstruct at least one characteristic of the ultrasound source.

2. The method of claim 1 wherein scanning the target surface comprises scanning a two-dimensional target surface, and wherein processing the measured hologram to reconstruct at least one characteristic of the ultrasound source comprises reconstructing three-dimensional acoustic field characteristics of the ultrasound source.

3. The method of claim 1 wherein obtaining a transducer operation characteristic comprises obtaining at least one of a linear, nonlinear, pulsing, continuous, spatial extent, Q-factor, or operating frequency characteristic of a radiating transducer.

4. The method of claim 1 wherein obtaining a holography system measurement characteristic comprises obtaining at least one of a size of a hydrophone sensing region, a hydrophone bandwidth, a geometry of a test tank, a liquid temperature in the test tank, or a reference position relative to a transducer at which the hydrophone is initially located.

5. The method of claim 1 wherein instructing the control computer to determine holography measurement parameters comprises instructing the control computer to determine at least one of a scanning position, a scanning extent, or a step size of a hologram sensor; a duration of measurement acquisition of a data recorder; or a duration or amplitude of excitation of the ultrasound source.

6. The method of claim 1 wherein scanning the target surface comprises continuously scanning the target surface.

7. A method of characterizing an ultrasound source using acoustic holography, the method comprising:
    obtaining a transducer geometry characteristic, a transducer operation characteristic, and a holography system measurement characteristic,
    instructing a control computer to determine holography measurement parameters;
    based on the holography measurement parameters, scanning a target surface to capture waveform measurements at a plurality of points on the target surface;
    using the waveform measurements to define a measured hologram at the target surface; and
    processing the measured hologram to reconstruct at least one characteristic of the ultrasound source,
    wherein processing the measured hologram to reconstruct a characteristic of the ultrasound source comprises using the hologram to define a boundary condition of the ultrasound source.

8. The method of claim 7 wherein processing the measured hologram comprises applying at least one of a Rayleigh integral, a Helmholtz-Kirchoff integral, a Khokhlov-Zabolotskaya-Kuznetsov equation, or a Westervelt equation.

9. The method of claim 1 wherein characterizing the ultrasound source comprises characterizing an acoustic field generated by the ultrasound source in uniform or nonuniform media.

10. A method of characterizing an ultrasound source using acoustic holography, the method comprising:
    obtaining a transducer geometry characteristic, a transducer operation characteristic, and a holography system measurement characteristic,
    instructing a control computer to determine holography measurement parameters;
    based on the holography measurement parameters scanning a target surface to capture waveform measurements at a plurality of points on the target surface;
    using the waveform measurements to define a measured hologram at the target surface; and
    processing the measured hologram to reconstruct at least one characteristic of the ultrasound source,
    wherein processing the measured hologram to reconstruct a characteristic of the ultrasound source comprises determining at least one of an acoustic output power of the ultrasound source or a radiation force that would occur if an acoustic beam from the ultrasound source impinged on a particular physical target.

11. The method of claim 10, further comprising using radiation force in conjunction with an independent radiation force balance measurement to calibrate a hydrophone's sensitivity at a single frequency.

12. A method for calibrating a hydrophone, the method comprising:
    using an uncalibrated hydrophone to measure a hologram for a source operating in continuous-wave mode at a specified output level;
    making a radiation force balance measurement of the source using a physical target;
    using the measured hologram to calculate a radiation force on the physical target as a function of hydrophone sensitivity; and
    calculating a hydrophone sensitivity by equating the radiation force balance measurement with the radiation force calculation based on the measured hologram.

13. The method of claim 12 wherein the using the uncalibrated hydrophone to measure the hologram comprises:
    obtaining a transducer geometry characteristic, a transducer operation characteristic, and a holography system measurement characteristic;
    instructing a control computer to determine holography measurement parameters; and
    based on the holography measurement parameters, obtaining a hologram.

14. The method of claim 12 wherein making the radiation force balance measurement of the source using a physical target comprises making a radiation force balance measurement under identical pulse waveform conditions for which the hologram was measured.

15. A holography system, comprising:
an ultrasound source;
a hologram sensor; and
a physical computer-readable storage medium having stored thereon, computer-executable instructions that, if executed by a computing system, cause the computing system to perform operations comprising:
determining holography measurement parameters;
receiving data related to a geometry characteristic, an operation characteristic, and a measurement characteristic of the holography system;
instructing the hologram sensor to measure acoustic waveforms generated by the ultrasound source; and
generating one or more of the acoustic propagation projections, radiation force calculations, or true power calculations based on a combination of the acoustic waveforms and the characteristics.

16. The holography system of claim 15 wherein the ultrasound source comprises a waveform generator, an amplifier, and a transducer.

17. The holography system of claim 15 wherein the hologram sensor comprises one or more of a two-dimensional array of independent hydrophones, a one-dimensional array of independent hydrophones in conjunction with a repeatable source and a positioner that is automated in at least one dimension, or a single hydrophone in conjunction with a repeatable source and a positioner that is automated in at least two dimensions.

18. The holography system of claim 15, further comprising:
an acoustic medium through which ultrasound waves travel from the ultrasound source; and
a thermometer configured to obtain a temperature of the acoustic medium.

* * * * *

UNITED STATES PATENT AND TRADEMARK OFFICE
CERTIFICATE OF CORRECTION

PATENT NO. : 9,588,491 B2
APPLICATION NO. : 13/894333
DATED : March 7, 2017
INVENTOR(S) : Oleg A. Sapozhnikov et al.

Page 1 of 1

It is certified that error appears in the above-identified patent and that said Letters Patent is hereby corrected as shown below:

On the Title Page

On the page 2, in Column 1, under "Other Publications", Line 53, delete "(ISTD)," and insert -- (ISTU), --, therefor.

On the page 2, in Column 2, under "Other Publications", Line 1, delete "Fouries" and insert -- Fourier --, therefor.

On the page 2, in Column 2, under "Other Publications", Line 53, delete "hyperecho" and insert -- hyperechoic --, therefor.

In the Specification

In Column 8, Line 8, delete "-Kirchoff" and insert -- -Kirchhoff --, therefor.

In the Claims

In Column 10, Line 10, in Claim 8, delete "-Kirchoff" and insert -- -Kirchhoff --, therefor.

In Column 10, Line 23, in Claim 10, after "parameters" insert -- , --.

Signed and Sealed this
Twenty-third Day of May, 2017

Michelle K. Lee
*Director of the United States Patent and Trademark Office*